United States Patent [19]

Miller et al.

[11] Patent Number: 4,585,652
[45] Date of Patent: Apr. 29, 1986

[54] ELECTROCHEMICAL CONTROLLED RELEASE DRUG DELIVERY SYSTEM

[75] Inventors: Larry L. Miller, Minneapolis, Minn.; Ronald L. Blankespoor, Grand Rapids, Mich.; Baruch Zinger, Rehovot, Israel

[73] Assignee: Regents of the University of Minnesota, Minneapolis, Minn.

[21] Appl. No.: 673,522

[22] Filed: Nov. 19, 1984

[51] Int. Cl.$^4$ .................................. A61K 31/745
[52] U.S. Cl. ............................ 424/83; 204/180.1; 204/228; 204/301; 424/14; 424/16; 424/19; 424/DIG. 7; 604/890; 604/891
[58] Field of Search ................. 128/1 R, 783, 784; 204/180.1, 228, 301; 424/14, 16, 19, 25, DIG. 6, DIG. 7, 83; 604/890, 891

[56] References Cited

U.S. PATENT DOCUMENTS

| | | | |
|---|---|---|---|
| 3,991,755 | 11/1976 | Vernon et al. | 128/172.1 |
| 4,140,121 | 2/1979 | Kühl et al. | 604/891 |
| 4,400,250 | 8/1983 | Fairhurst | 204/301 |
| 4,506,680 | 3/1985 | Stokes | 604/891 |

OTHER PUBLICATIONS

A. N. K. Lau and L. L. Miller, J. Amer. Chem. Soc., 105, 5271 (1983).
A. N. K. Lau et al., J. Amer. Chem. Soc., 105, 5278 (1983).
L. L. Miller et al., Neuroscience Letters, 35, 101 (1983).
L. R. Faulkner, Chem. Eng. News (Feb. 27, 1984) at pp. 31–35.
P. Burgmayer and R. W. Murray, J. Electroanal. Chem., 147, 339 (1983).
P. Burgmayer and R. W. Murray, J. Phys. Chem., 88, 2515 (1984).
P. Burgmayer and R. W. Murray, J. Amer. Chem. Soc., 104, 6139 (1982).
Anon., Chem. Eng. News (Sep. 10, 1984) at pp. 38–39; Polyaniline Used in Rechargeable Batteries.

Primary Examiner—John F. Niebling
Assistant Examiner—Terryence Chapman
Attorney, Agent, or Firm—Merchant, Gould, Smith, Edell, Welter & Schmidt

[57] ABSTRACT

A method is disclosed for the controlled delivery of an ionic bioactive chemical into a physiological medium comprising ionically binding the chemical to redox sites on a charged polymer and releasing the bound chemical into the medium by neutralizing the charge on the polymer.

20 Claims, 4 Drawing Figures

ELECTROCHEMICAL CONTROLLED RELEASE DRUG DELIVERY SYSTEM

U.S.P.H.S. and N.S.F. SUPPORT

This invention was made with Government support under Contract Number 5-R01-GM-24493, awarded by the U.S. Public Health Service and Contract Number CHE-8203493, awarded by the National Science Foundation. The Government has certain rights in the invention.

BACKGROUND OF THE INVENTION

The controlled release of bioactive substances such as drugs has become an important mode of treatment for many diseases and disorders. Pharmaceutical manufacturers have introduced many products which are designed to gradually release bioactive substances at a therapeutically-useful rate and to spatially target the release. For example, the release rate may be controlled mechanically by a valving system, or physically, as by slow drug diffusion through protective encapsulation.

Iontophoresis is an electrochemical process which has found limited utility for the controlled application of charged agents such as metal ions, analgesics and anesthetics to afflicted bodily areas such as inflamed joints. Iontophoresis utilizes direct electrical current to drive ionized chemicals through the intact skin. For example, in aqueous media, sodium salicylate disassociates into ions. The salicylate ions responsible for the analgesic action of the salt are negatively charged. Accordingly, these active species can be driven through the skin by the repelling action of a cathodic current which is applied to a reservoir containing the active species. Thus, when ion-tophoresing salicylate through the skin, the electrode contacting the salicylate solution must be connected to the positive pole of a battery while the counter-electrode which contacts the skin at some remote point is connected to the negative pole to provide a return path for the current. Simple circuits effective to conduct ion-tophoresis are disclosed in U.S. Pat. No. 3,991,755, the disclosure of which is incorporated by reference herein.

However, special difficulties are encountered in therapeutic or experimental situations where it is desired to release discrete units of highly active agents in vivo. For example, in neuroscience, it is important to be able to deliver neurotransmitters or drugs to specific locations at specific times. In this way, the effect of these compounds on single neurons can be studied. Iontophoresis has been employed for drug delivery at the single neuron level, whereby a solution of an active electrolyte is placed in a micropipet and then "phoresed" out with a small current. Although widely used, this technique suffers from a number of disadvantages, primarily related to quantification control. It is also necessary to apply the active substance in combination with a relatively large quantity of a carrier liquid to the area to be treated or tested.

One electrochemical alternative to iontophoresis is presented by L. L. Miller et al. in *Neuroscience Letters*, 35, 101 (1983) and *J. Amer. Chem. Soc.*, 105, 5271, 5278 (1983), who disclose electrodes which are used to deliver the neutral neurotransmitters dopamine (3, 4-dihydroxy-phenethylamine), glutamic acid and gamma-aminobutyric acid from their surfaces in response to an electrical signal. A compound electrode was constructed by coating an inert electrode with a polystyrene-based polymer film having the neutrotransmitter covalently bound to the polymer backbone through an amide linkage. At sufficiently negative potentials, cathodic reduction cleaved the amide bond and released the neurotransmitter into a small volume of aqueous buffer. The released amine was detected at a second electrode by its electrochemical oxidation or alternatively, analyzed by HPLC. Although this method permitted the release of a bioactive agent into a physiological medium, the amounts released at neutral pH were vey low, and could not be appreciably increased by increasing the amount of loaded polymer on the electrode, due to slow charge propagation within the film.

The use of such polymers for drug delivery is disadvantageous, since a separate chemical synthesis is required to incorporate the active species into the polymer. Furthermore, polymers bearing covalently-bound drugs cannot be easily reloaded once the drug has been released from the polymeric matrix. Therefore, a need exists for a electrochemical method for the controlled delivery of charged bioactive chemical species from an electrode into physiological media such as blood, lymph, spinal fluid and the like.

BRIEF DESCRIPTION OF THE INVENTION

The present invention is directed to controlled release drug delivery systems which employ an electrode comprising a polymer which can be electrochemically cycled between the charged and the neutral, or insulating states. In the charged, or ionic state, the polymer can be loaded with bioactive counterions. When the charge on the polymer is neutralized or reversed, the counterions are released into the surrounding medium and become available to perform their intended function, e.g. to exert their pharmacological activity.

In practice, a body of the conductive polymer can be employed to form the active portion of a working electrode. The polymer is then charged cathodically or anodically while in contact with an aqueous medium containing the desired drug counterion causing it to ionically-bind a pharmaceutically-effective amount of the counterions. The drug-loaded electrode is then contacted with a physiological medium. As used herein, the term physiological medium is intended to refer to an electrolytic solution which is either a naturally-occurring body fluid such as blood, lymph, cerebrospinal fluid or the like, or which is formulated to approximate the properties of such fluids. For example, the electrode may be implanted in a natural or artifically-formed body cavity or placed in contact with the skin, mucous membranes or the like. The drug counterions can then be released in vivo in a controlled fashion by one or more quantified current pulses.

For example, these polymers can be loaded with anionic compounds which are bioactive, such as amino acids, by converting the polymer into the oxidized or electropositive state with an anodic current in the presence of dissolved amino acid carboxylate salts. Once loaded, one or more cathodic pulses can be employed to electrically neutralize the polymer, resulting in the release of all or a part of the bioactive counteranions into the desired medium. The polymer can be removed from the delivery locale, reloaded and reused if desired. The unit dosage of the bioactive compound can be controlled by adjusting parameters such as the release pulse strength and duration, the loading concentration and the electrode conformation and position.

DETAILED DESCRIPTION OF THE INVENTION

Preparation and Loading of Electroactive Polymers

Polymers useful in the present invention are those organic or organometallic polymers which (a) comprise functional groups which can be electrochemically cycled between the charged and neutral states and (b) possess the physical properties required for use as working electrodes. These polymers are preferably stable in air and water, highly conductive and processable.

In the charged state, these polymers can attract and retain oppositely-charged, pharmaceutically-effective amounts of bioactive chemical species. The ionically-bound species can be released from the polymeric matrix when the polymeric charge is neutralized. For example, polymers which comprise cationic sites in the charged state can be loaded with bioactive anions which are delivered by employing a cathodic current to neutralize the positively charged polymer, while polymers which comprise anionic sites which charged can be used to bind and release active species which are cationic.

Such charged polymers may be considered as belonging to two broad classes: (a) those comprising redox sites which are covalently bound to an electrically inactive backbone, such as poly(vinylferrocene); and (b) those having redox sites integrally-incorporated into the polymeric backbone. The latter type will be referred to herein as "conductive polymers". For a general discussion of these two classes of charged polymers, see L. R. Faulkner, *Chem. Eng. News* (Feb. 27, 1984) at pages 31–35, the disclosure of which is incorporated by reference herein.

Conductive polymers can be switched from the charged (conductive) and nonconducting (neutral) states by employing an electric current to alternately reduce and oxidize the polymer chain. Although the redox sites on polymers of type (a) can also be electrochemically oxidized and reduced, these polymers cannot readily pass current by electron transfer along the backbone. Conductive polymers, on the other hand, permit direct electron transfer along the polymeric chains, preferably via a pi-electron network. When such polymers are electrically neutral, the bonding states in the pi-electron network are full and electronic conductivity is very low. The removal of pi-electrons creates cationic vacancies that permit current to flow along the chains, while addition of pi-electrons to vacancies in neutral systems can produce anionic sites.

Since these polymers are essentially metallic in character, they can be designed to bear high charge densities and exhibit efficient charge transfer. Furthermore, they need not be bound to a conductive electrode surface in order for the redox sites to be charged and discharged, but can be formed into free-standing bodies which can function as working electrodes when connected to a current source.

Cationic charged polymers such as those comprising unsaturated carbocyclic or heterocyclic rings such as phenyl, pyrrole, pyridyl, cyclopentadienyl and thiafulvalenyl can be used in the invention. Preferably the rings will be linked into a continuous conjugated, pi-electron network, such as those present in polyaromatic or poly-(pseudo-aromatic) systems. One preferred class of conductive polymer is the polypyrroles, which are formed by the electrochemical oxidation of a pyrrole as described by A. F. Diaz et al. in *J. Chem. Soc. Chem. Commun.*, 635, 854 (1979).

Polythiophene and several beta-substituted polythiophenes have been prepared by electrochemical oxidation and polymerization of their respective monomers. These polymers can be repeatedly cycled between a conductive oxidized state and a semi-conductive neutral state. See G. Tourillon, *J. Electroanal. Chem.*, 161, 51 (1984). Although their stability in aqueous media indicates that these polymers might be useful to deliver anionic drugs, their high oxidation potentials (greater than 0.70 V vs. SCE) would eliminate the delivery of drugs that are electroactive in this potential region. The beta-substituted-thiophene, poly-3-methoxythiophene was prepared and found to possess a significantly lower oxidation potention. This material can be employed to deliver anions such as amino acid carboxylates according to the method of this invention.

Other conductive polymers useful to bind and release anions include substituted poly(pyrroles), substituted polythiophenes and similar poly(heterocyclic) materials. Other useful conductive polymers include polyanilines, poly(thiophenols), poly(aromatics) or polyacetylenes. For example, see *Chem Eng. News* (Sept. 10, 1984) at pages 38–39. Conductive polymers useful for the delivery of cations can also come from the classes of polyacetylenes as well as polyaromatics or poly(-heteroaromatics). For example, poly(9-phenylquinoline) would be charged negatively to hold cations, then discharged.

Redox polymers of the type (a) which can be used to deliver bioactive anionic species include polymers holding a variety of cationic metal complexes either electrostatically or covalently. Examples include organic polymers with pendant ligands such as cyclopentadienyl, pyridine, bipyridine, tripyridine, primary amines, porphyrins, phthalocyanines and related macrocyclic ligands. These ligands can bind a wide variety of metal ions including iron, cobalt, ruthenium, osmium which are capable of rapid electron transfer reactions between the redox centers. Organic polymers which could be used as anion delivery agents include those with pendant groups that are relatively stable in both the oxidized and reduced forms, like tetrathiofulvalene, aromatic diamines, cationic dyes such as those from the classes thiazines, diazines, oxazines, triarylmethanes, cyanines, mercocyanines and the like. Polymers of type (a) useful for cation delivery include metal complexes with a net negative charge like sulfonated complexes or oxyanions like the conjugate anion of a hydroquinone or an enolate. Carboxylated or sulfonated aromatics could also be useful, especially when the aromatic moiety is substituted by nitro, carbonyl, or sulfonyl. Anionic dyes of interest may be selected from anionic cyanines, oxonoles, quinones, and the like.

The charged polymers can be employed to form working electrodes by electrochemically oxidizing or reducing a solution of appropriate monomer so as to deposit a coating of the charged polymer on the surface of a conventional electrode. If the monomer can be polymerized in the presence of the desired counterion, it will be deposited in the loaded condition. If the monomer will not polymerize electrochemically in the presence of the desired counterion, the undesired counterion may be exchanged for the desired species by cycling the polymeric electrode between the neutral and charged stage in contact with a medium containing an excess of the desired counterions. In this manner, the undesired ions are forced out and replaced with the desired ions.

Working electrodes comprising the present charged polymers can be formed in a wide variety of sizes, from microelectrodes of about 1 uM$^2$ to electrodes designed to encompass an inflamed joint or to cover a large area of a patient's skin. In many cases it will be desirable to coat inert substrates of high surface area with the charged polymer, in order to increase the reservoir of the active species bound thereto. Implantable electrodes, or those designed for parenteral drug delivery can be fabricated from polymer coated screens or mesh, or could consist essentially of appropriately-shaped bodies of the conductive polymeric material. The screens or mesh may be composed of a wide variety of conducting materials including metals or carbon fibers.

Especially preferred polymers for use in the present invention are those which are soluble in organic solvents in either the charged or neutral state. These polymeric solutions can be used to form films of controlled thickness by applying coatings of the solutions to conductive electrode substrates, as by dip- or spin coating and then evaporating the carrier solvent. For example, the reduced form of poly-3-methoxythiophene is soluble in acetonitrile, methylene chloride, acetone and dimethyl formamide (DMF) while the oxidized form is soluble in DMF.

Bioactive Counterions

The present drug-delivery method is generally applicable to the release of ionic materials such as organic cations and anions. Anionic bioactive species useful as counterions include the pharmaceutically-acceptable salts of carboxylates, phosphates, sulfates, bisulfites, and the salts of acidic N-H moieties such as amides. Many useful drugs containing these functional groups are commercially available as their water-soluble alkali metal or alkaline earth metal salts, most commonly as sodium, lithium, potassium, magnesium or calcium salts.

Useful bioactive organic carboxylate salts include sodium ethacrynate, levothyroxine sodium, valproate sodium, magnesium salicylate, clorazepate sodium, sodium folate, leucovorin calcium, sodium ascorbate, cephaprin sodium, cephalothin sodium, penicillin G potassium, dextrothyroxine sodium and the carboxylate salts of amino acids. Many carboxylic acid-containing drugs can be converted into pharmaceutically-acceptable water-soluble salts by conventional techniques, including aspirin, prostaglandins, retinoic acid, furosemide, tricrynafen, probenicid and the like.

Also useful as anionic counterions are phosphate salts such as cortisol sodium phosphate, menadiol sodium phosphate, etidronate disodium phosphate, triclofos sodium and the like; sulfates such as estrone potassium sulfate and heparin sodium; bisulfites such as menadione sodium bisulfite and the salts of acidic amines such as purines and amides, including sulfacetamide sodium, tolbutamide sodium, sulfadiazine sodium and the salts of aminophylline, theophylline and the like.

Bioactive cationic species include the pharmaceutically-acceptable salts such as the halide, nitrate and methylsulfate salts of quaternary amines and charged sulfur and nitrogen-containing heterocyclic drugs, such as those comprising thiazinium, pyridinium, pyrrolidinium, thiazolium or piperidinium salts. Drugs comprising quaternary amines include gallamine triethiodide, metocurine iodide, hexafluorenium bromide, decamethonium bromide, pancuronium bromide, succinyl choline chloride, neostigmine bromide, demacarcium bromide, amberonium chloride, diphemanil methyl sulfate, choline chloride, and the like. Useful heterocyclic salts include thiamine nitrate, methylene blue, trimethaphan camsylate, cetylpyridinium chloride and pyridostigmine bromide.

Neutral, pharmacologically-active species may also be loaded and released via the electroactive polymers if they are first modified to introduce suitable ionic functional groups, such as the above-mentioned phosphates, sulfates, quaternarized nitrogen and the like. Techniques for introducing such polar groups are well-known and widely-employed to increase the water-solubility of drugs which are nonsoluble or only sparingly soluble in water, so that they may be orally administered. Such techniques include the conversion of hydroxyl groups to halides and then to phosphonoxy or phosphinoxy groups, and the conversion of hydroxyl groups to the salts of half esters. Bisulfites may be formed by the conjugate addition of bisulfite salts to alpha, beta-unsaturated ketones, and amines may be quaternized with alkyl halides.

Controlled Drug Release Systems

Figure 1:
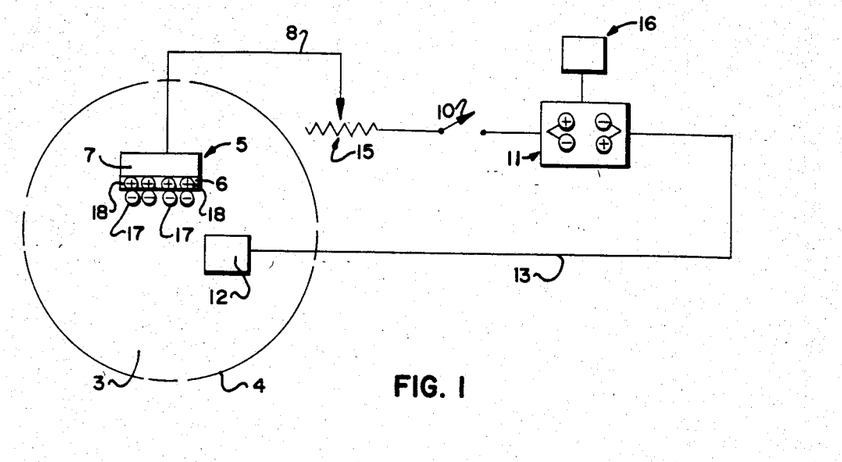
FIG. 1 is a simplified illustration of one embodiment of a drug delivery system of the present invention.
Figure 2:
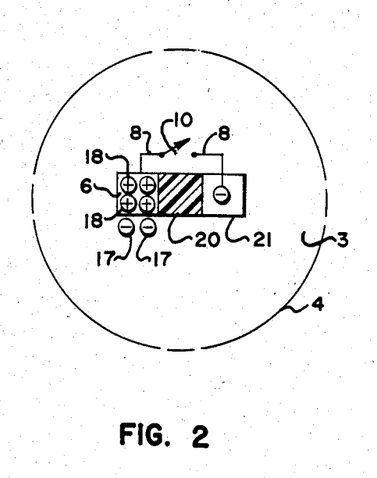
FIG. 2 is a simplified illustration of an embodiment of a self-contained drug system of the present invention.

Devices useful for the controlled delivery of bioactive ions into physiological media such as mammalian fluids or tissues, are schematically depicted in FIGS. 1 and 2.

In the simplified form illustrated in FIG. 1, the drug delivery device incorporates working electrode 5 which, as illustrated, comprises a coating of the charged polymer 6 on an inert conductive body 7. Body 7 may be formed of any physiologically inert substance, e.g. glassy carbon, graphite, gold, silver, platinum and the like. Body 7 is connected by wire 8 to a means capable of charging or discharging the polymer, such as power supply 11 which may be a battery or other suitable DC source, via switch 10 and variable resistor 15. The polarity of the current produced by power supply 11 may be reversed by a polarity control 16. Power supply 11 is also connected via wire 13 to counterelectrode 12. In use, electrodes 5 and 12 can be contacted with a body of physiological medium 3, such as spinal fluid, blood, lymph, fatty tissue and the like, by positioning the electrodes in or abutting the appropriate body structure 4. Except in the case of miniaturized units intended for long-term in situ drug delivery, remote powering and switching of the device is desirable. The variable resistor permits the current to be controlled. The power supply could also incorporate more sophisticated current delivery apparati, such as pulse generators, counters and recorders.

FIG. 2 illustrates in simplified form a self-contained drug delivery device suitable for implantation in a body of physiological medium 3 in a body structure 4. The working electrode is formed from a body of charged polymer 6 which is connected by wire 8 to current supply means 21. In this device, current supply means 21 comprises an electrode formed of a material having sufficient electrochemical potential with respect to charged polymer 6 that it will supply a current flow adequate to neutralize the charged sites 18 on polymeric electrode 6 when both electrodes are contacted with physiological medium 3. In this device, working electrode 6 will preferably be separated from the current-supplying electrode 21 by an insulator 20, which may be formed from a body of insulating polymer. As depicted, the current-supplying electrode 21 is negatively charged, and may be formed from a reducing agent such as a negatively charged polyacetylene or a metal such as zinc. Of course, organic or inorganic materials capable of inducing an anodic current flow could also be employed to form electrode 21. In the resting state in the devices shown in both FIGS. 1 and 2, switch 10 would be open, and the current would be off. When closed, the anodic or cathodic current flow initiates the delivery of the desired bioactive ions 17, which are ionically bound to the polymer to the desired concentration. As depicted, polymer 6 comprises cations 18 which ionically bind bioactive anions 17. In the implanted device shown in FIG. 2, switch 10 can be remotely activated so that the ion delivery can be initiated or interrupted without the need for surgical procedures.

The invention will be further described by reference to the following detailed examples.

EXAMPLE I

Controlled Release of Glutamate Anions From Polypyrrole Films

Polypyrrole was anodically deposited to a thickness of approximately 5 uM onto a glassy-carbon rod electrode from an aqueous solution containing sodium perchlorate. This coated electrode, which exhibited voltammetric properties similar to those reported by Diaz et al., cited hereinabove. The coated electrode was rinsed with water and transferred to an aqueous solution containing only sodium glutamate (0.1M, pH=6.95). A potential/time square wave was applied between the limits of 0.0 V and $-1.0$ V (SCE). At $-1.0$ V the film was reduced; at 0.0 V, it was reoxidized. The cyclic voltammogram of the coated electrode was altered by this procedure, and could be restored to its original shape in a perchlorate solution.

The glutamate-loaded electrode was transferred to an aqueous sodium chloride solution where a 2.0 minute cathodic pulse ($-1.0$ V) was effective to release glutamate anions. The electrode was then reloaded, washed and glutamate again released into the same solution. Amino acid analysis showed that $2.7 \times 10^{-8}$ mol cm$^{-2}$ of electrode area of glutamate anions had been released. This is about 200 times the amount released by the reductive release of covalently-bound glutamic acid as described hereinabove.

In a control experiment, the loaded electrode was prepared and exposed to aqueous NaCl in the absence of current passage. Only $1.9 \times 10^{-9}$ mol cm$^{-2}$ of glutamate was released.

EXAMPLE II

Ferricyanide Release from Polypyrrole Films

Figure 3:
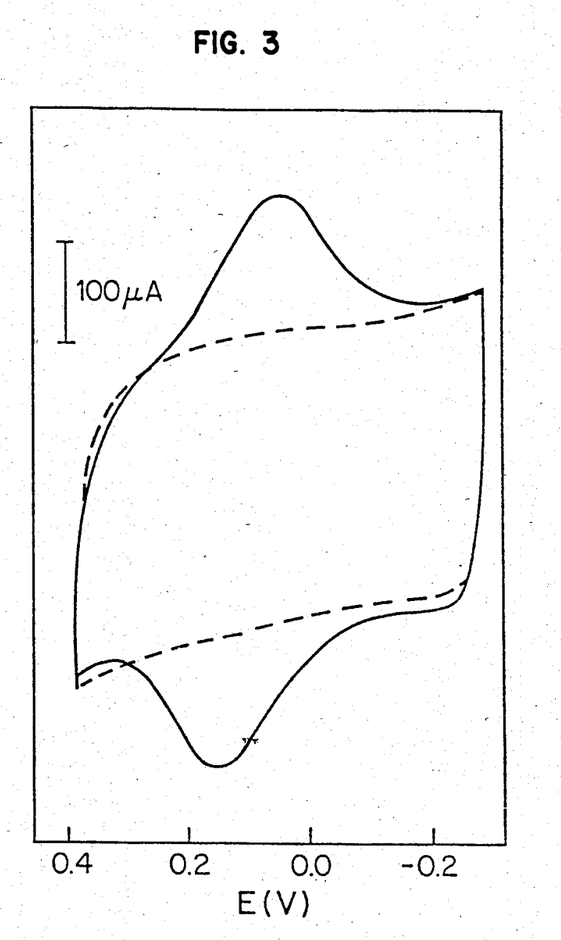
FIG. 3 depicts cyclic voltammograms recorded for an electrode comprising a conductive polypyrrole film, with and without bound ferricyanide.

To study ferricyanide anion (FCN) release from polypyrrole films, the films were deposited from aqueous 0.05M sodium chloride solutions that were 0.05M in pyrrole and 0.01–0.03M in FCN, by anodic oxidation at 0.7 V onto glassy carbon electrodes. The coated electrode was transferred to an aqueous solution containing only the NaCl electrolyte and a typical cyclic voltammogram (film thickness=1 uM) is shown in FIG. 3. Well defined waves for the FCN redox couple (solid curve) are superimposed on the large polypyrrole (PP) background. Integration of the peak current gave an estimated value for the amount of electroactive FCN in the polymer as $3.2 \times 10^{-8}$ mol cm$^{-2}$. The FCN redox waves were stable to cycling within potential range of $-0.3$ to $+0.4$ V, and after 17 hr in buffered pH 7 solution the peak current maintained 94% of its initial height. Stepping the potential for ca. 2 min to $-1.0$ V caused a dramatic change in the voltammetric response of the film. The redox couple of FCN at about 0.1 V disappeared (FIG. 3 dashed line) indicating the release of FCN anions during the reduction of the film.

The crucial experiments involved measuring the amount of FCN released and demonstrating that the amounts released could be completely controlled. A four electrode small volume (droplet) cell was constructed employing a ring (Pt)-disc (GC) electrode. The cell structure was otherwise as described in *Neurosci. Letters*, 35, 101 (1983), the disclosure of which is incorporated by reference herein. The disc had been previously coated with PP/FCN film. A constant potential pulse ($-0.8$ V vs Ag/AgCl) was applied to the disc for 2 min. The ring was then made the working electrode, and by cycling the potential of the ring from $-0.1$ to $+0.6$ V, FCN was released as desired. In a control experiment the cell was assembled as usual, but no current was passed. No FCN was found in solution. Hence the release of FCN is triggered by the reduction of the film. No evidence for a spontaneous ion exchange between FCN in the film and other anions in the solution was found.

In further experiments, the amount of FCN released was quantitated in various film thickness. The results shown in Table I indicate that the amount of released material was proportional to the thickness of the film, when the thickness was less than 1 uM.

TABLE I

| Yield of FCN released from GC/PP/FCN Polymer[a] | | |
|---|---|---|
| Film Thickness[b] ($\mu$M) | Yield (nmol cm$^{-2}$)[c] | Conc (mM)[d] |
| 0.11 | 2.58 | 0.024 |
| 0.53 | 10.2 | 0.094 |
| 0.52 | 10.5 | 0.096 |
| 1.05 | 20.3 | 0.173[e] |
| 0.98 | 19.8 | 0.182 |
| 3.31 | 38.1 | 0.35 |
| 3.36 | 46.5 | 0.43 |

Figure 4:
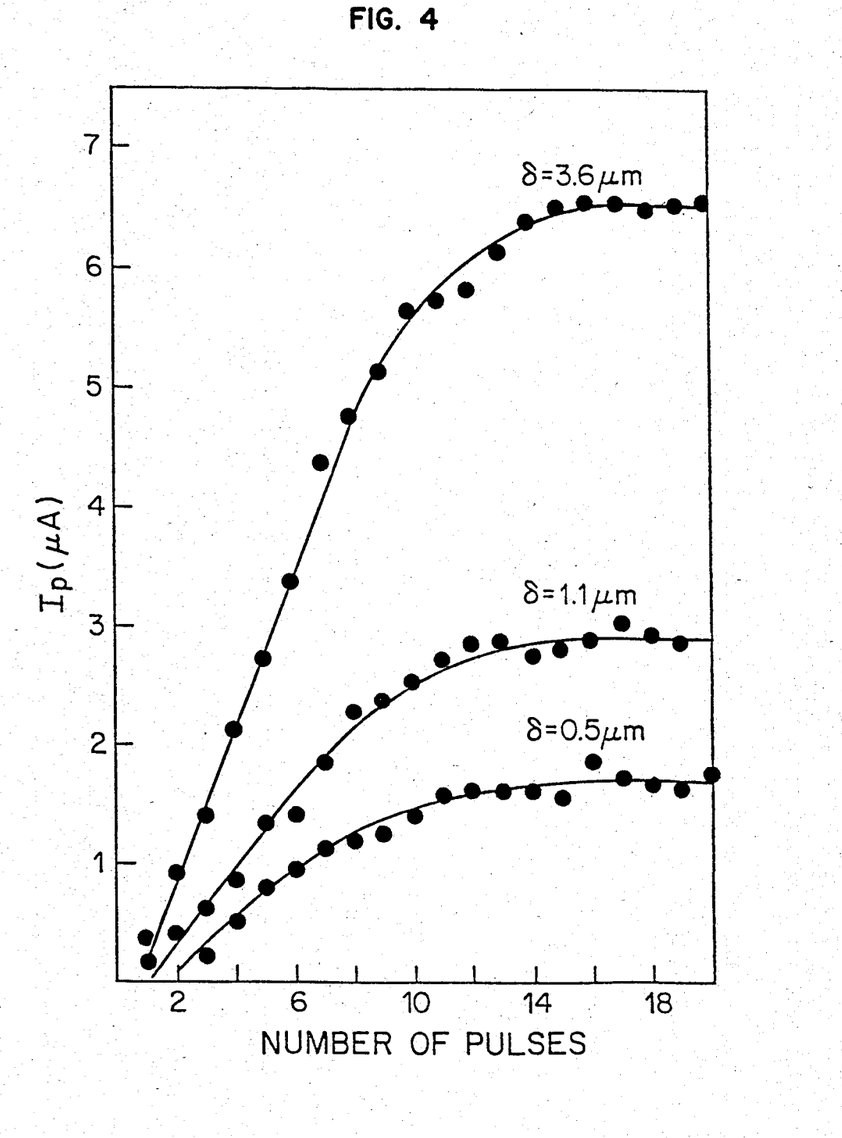
FIG. 4 is a graphic depiction of the profile of ferricyanide release from an electrode comprising a conductive polypyrrole film.

It was also of interest to apply short pulses to GC/PP/FCN and to check the amount of the released material to demonstrate quantitative control. Using the small volume cell (50 uL, 0.1M NaCl) the coated disc was pulsed for 1 sec (at $-0.8$ V). After each pulse a cyclic voltammogram (CV) using the ring was taken. In this way the profile of FCN concentration as a function of time was obtained. The results are shown in FIG. 4. The peak current from released FCN is plotted vs the number of pulses for different thickness of films. The amount of the released FCN increased to a constant value after about twelve pulses and the total amount of the released FCN after these twelve one-second pulses was in agreement with the amount found previously for a 2 min. pulse.

The results of Examples I and II clearly demonstrate that a polymeric film can be electrically controlled to intermittently release controlled amounts of the ionically-bound counteranions.

EXAMPLE III

Controlled Release of Glutamate Anions from Polymerized 3-Methoxythiophene

A cyclic voltammogram (CV) of 1.34 mM 3-methoxythiophene in $H_2O\text{-}CH_3CN$ (3:1) containing 0.01M $NaClO_4$ at a glassy carbon disk (A=0.090 cm$^2$) at a scan rate of 100 mVs$^{-1}$ exhibits an irreversible wave at $+1.32$ V (SCE). Constant potential oxidation of a 35.0 mM solution of 3-methoxythiophene at $+1.30$ V (SCE) in the same electrolyte for 10 sec. (Q=7.21 mC) resulted in the formation of a film on the electrode surface. This coated electrode was removed from the coating solution, dipped several times in water, and introduced into an aqueous 0.01M $NaClO_4$ solution. After 5-10 cycles between $+0.80$ and $-0.50$ V, reproducible steady-state cyclic voltammograms were recorded. As is the case with polythiophene and several of its derivatives, one oxidative wave and two rather broad reduction waves are observed, albeit at potentials nearly 700 mV less positive than those for polythiophene. As the scan rate was increased from 20 to 200 mVs$^{-1}$, the peak potential for the oxidative wave ($Ep_a$) increased from 310 to 420 mV, the peak current divided by the scan rate decreased from 2.375 to 1.568 uAs(mV)$^{-1}$, and the charge of the oxidative peak decreased from 0.529 to 0.472 mC.

Films of polymerized 3-methoxythiophene with varying thicknesses were prepared by varying the oxidation time. Both the oxidized and reduced states of polymerized 3-methoxythiophene are quite stable in the presence of oxygen and water. CVs of either film in aqueous $ClO_4^-$ are virtually identical before and after exposure to air for periods of 6-12 hr or after repeated cycling between $+0.80$ and $-0.50$ V. After 40 cycles in this potential range, only a 5% decrease in Q was observed. Surprisingly, it was found that the reduced film of polymerized 3-methoxythiophene, which is green in reflected light, is quite soluble in $CH_3CN$, $CH_2Cl_2$, acetone and DMF, forming deep red solutions. The oxidized form, which appears gold in reflected light, is not very soluble in $CH_3CN$, $CH_2Cl_2$, and acetone, but can be dissolved in DMF giving a deep blue solution.

The appreciable solubility of polymerized 3-methoxythiophene provides for the first time an alternate method for preparing films of this material. The processability of the polymer was demonstrated by dissolving the reduced film in $CH_2Cl_2$ and coating a glassy carbon electrode with the polymer by evaporation of the solvent. The electrochemical response of the coated polymer was essentially identical to that achieved before dissolution. CVs of films with varying thicknesses prepared in this manner were recorded in 2:1 $H_2O$—$CH_3CN$ containing 0.01M $NaClO_4$. From the Q of the oxidative wave taken with the assumption that the film is poly(3-methoxythiophene), the percentage of thiophene units in the film that are charged (e.g., level of doping) was calculated. The percentage decreased from 15 to 9 as the ug of polymer per cm$^2$ is increased from 21.6 to 140. A doping level of 25% has been reported for poly(3-methylthiophene) based upon elemental analysis by G. Tourillon et al., in *J. Electroanal. Chem.*, 161, 51 (1984).

Polymerized 3-methoxythiophene was successfully employed as a vehicle for delivery of negatively charged drugs. The CV indicates that the polymer can be doped with the neurotransmitter glutamate as the counterion, but at a lower level than with perchlorate. To demonstrate that polymerized 3-methoxythiophene can load and unload glutamate by electrochemical pulsing, a glassy carbon rod with a surface area of 10.8 cm$^2$ was coated with the oxidized film to a capacity of 463 mC cm$^{-2}$. The coated electrode was dipped in water and transferred to an aqueous 0.10M glutamate solution where sequential potentials of $-0.50$, $+0.80$, $-0.50$, and $+0.80$ V were applied, each for 30 sec. This pulsing procedure replaces (at least in part) perchlorate in the film with glutamate. The oxidized electrode was removed, dipped in water, and washed by dipping in an aqueous solution of 0.10M $NaClO_4$ (Solution A) for two minutes. The coated electrode was transferred to a second aqueous solution of 0.10M $NaClO_4$ (Solution B) for another two-minute period. For the electrochemical unloading of glutamate, the coated electrode was transferred to a third aqueous 0.10M $NaClO_4$ solution (Solution C) which occupied the center compartment of a three-compartment cell. The compartments each contained 0.10M $NaClO_4$ and were separated by a glass frit and an aqueous agar (0.50M $NaClO_4$). A carbon sponge served as the counter electrode in the second compartment and the SCE reference electrode occupied the third compartment.

The potential of the coated electrode was pulsed at $-0.50$ V and back to $+0.80$ V as in the glutamate solution. The electrode was dipped in water and returned to the glutamate solution for reloading. This loading-unloading procedure was carried out a total of four times. Then, using an amino acid analyzer, solutions A, B, and C were found to contain 101, 12, and 224 ug of sodium glutamate, respectively. The data show that some glutamate is weakly bound and easily washed from the film. A larger quantity, however, is more strongly bound, and is only released by reduction of the film. Thus, polymerized 3-methoxythiophene can be used to deliver glutamate and the coated electrode can be readily reloaded. Furthermore, taking into account differences in electrode surface area, the average amount of glutamate released in each loading-unloading sequence was nearly 200 times greater than the amount of glutamate that was released from polystyrene polymers containing covalently bound glutamic acid.

This example indicates that polymerized 3-methoxythiophene satisfies the criteria for a useful drug delivery material. Furthermore, its solubility makes this material processable, in that coatings of the polymer can be applied to conductive substrates by applying solutions thereof and evaporating the carrier solvent.

It is expected that a wide variety conductive polymers can be prepared and employed for the controlled release of ionic organic pharmaceuticals of varying structure using techniques such as those set forth in the present Examples.

Although the invention has been described with reference to various specific and preferred embodiments and techniques, it should be understood that many variations and modifications may be made while remaining within the spirit and scope of the invention.

What is claimed is:

1. A method for the controlled delivery of an ionic bioactive chemical into a physiological medium comprising:
   (a) ionically binding said chemical to a polymeric body comprising oppositely-charged redox sites;
   (b) contacting said polymeric body with said physiological medium; and
   (c) releasing said bound chemical into said medium as an ionic species by neutralizing the charge on the polymeric body.

2. The method of claim 1 wherein said polymeric body is conductive.

3. The method of claim 2 wherein the charged polymeric body comprises cationic sites and is employed to bind anionic chemicals which are released by employing a cathodic current to neutralize the charge on the polymeric body.

4. The method of claim 3 wherein the charged polymeric body comprises oxidized polypyrrole or oxidized poly(beta-methoxythiophene).

5. The method of claim 2 wherein the charged polymeric body comprises anionic sites and is employed to bind cationic chemicals which are released by employing an anodic current to neutralize the charge on the polymeric body.

6. The method of claim 5 wherein the charged polymeric body comprises a reduced polyacetylene or a reduced, modified polyquinone.

7. The method of claim 1 wherein an electrode comprising said polymeric body is employed to bind said chemical by charging said electrode in contact with a solution of said ionic chemical.

8. The method of claim 7 wherein the ionic chemical is intermittently released by neutralizing the charge on the polymeric body with a plurality of quantified pulses of current.

9. The method of claim 8 wherein said bound chemicals are released in vivo.

10. The method of claim 9 wherein said electrode is implanted in a patient's body cavity or attached to the patient's skin.

11. The method of claim 1 wherein said ionic bioactive chemical is the anion of a pharmaceutically-acceptable salt selected from the group consisting of phosphate, sulfate, bisulfite, carboxylate and acidic N—H group salts.

12. The method of claim 1 wherein said ionic bioactive chemical comprises a quaternary ammonium cation.

13. The method of claim 12 wherein said ionic bioactive chemical is the cation of a pharmaceutically-acceptable salt selected from the group consisting of thiazinium, pyridinium, pyrrolidinium, thiazolium and piperidinium salts.

14. A system for the controlled release of a bioactive ionic chemical into a physiological medium comprising:
   (a) a working electrode comprising a charged conductive polymer;
   (b) a bioactive ionic chemical ionically bound to said electrode; and
   (c) means comprising a power supply of reversible polarity which is capable of charging or discharging said polymer by delivering an anodic or cathodic current thereto.

15. The system of claim 14 wherein said electrode comprises a coating of said conductive polymer on an inert, conductive substrate.

16. The system of claim 14 wherein the electrode consists essentially of said conductive polymer.

17. The system of claim 14 wherein said polymer comprises a continuous, conjugated pi-electron network.

18. The system of claim 14 further comprising a variable resistor between said current supply means and said electrode effective to control the magnitude of the current.

19. The system of claim 14 wherein said current supply means comprises an electrode having sufficient electrochemical potential with respect to the working electrode to discharge the charged working electrode when both electrodes are contacted with a physiological medium.

* * * * *

UNITED STATES PATENT AND TRADEMARK OFFICE
CERTIFICATE OF CORRECTION

PATENT NO. : 4,585,652
DATED     : April 29, 1986
INVENTOR(S) : Larry L. Miller et al.

It is certified that error appears in the above-identified patent and that said Letters Patent is hereby corrected as shown below:

At Column 2, line 11, for "vey" read --very--.

At Column 3, line 33, for "which" (second occurrence),
    read --when--.

At Column 8, line 55, insert
    --a The disc was pulsed for 2 min at -0.8 V (vs. Ag/AgCl 3M
        KCl). The volume of the electrolyte droplet was 50 uL.
    b The thickness was estimated taking 24 mC cm$^{-2}$ equivalent
        to 0.1 um.
    c Surface concentration of the FCN.
    d Solution concentration of FCN after release.
    e The volume of electrolyte droplet was 70 µL.--.

Signed and Sealed this

Fourteenth Day of October, 1986

[SEAL]

*Attest:*

DONALD J. QUIGG

*Attesting Officer*     *Commissioner of Patents and Trademarks*